United States Patent [19]

Tamura et al.

[11] 4,221,908
[45] Sep. 9, 1980

[54] ANTIBACTERIAL COMPOUNDS AND PROCESS FOR PRODUCTION THEREOF

[75] Inventors: Gakuzo Tamura; Kenichi Shimizu, both of Tokyo, Japan

[73] Assignee: Kyowa Hakko Kogyo Co., Ltd., Tokyo, Japan

[21] Appl. No.: 30,659

[22] Filed: Apr. 16, 1979

Related U.S. Application Data

[62] Division of Ser. No. 878,776, Feb. 17, 1978.

[30] Foreign Application Priority Data

Feb. 18, 1977 [JP] Japan .................................. 52-16068

[51] Int. Cl.² .................. C07D 207/20; C07D 207/24
[52] U.S. Cl. ..................................... 542/426; 424/116; 424/274; 424/123; 542/427
[58] Field of Search ................ 542/426, 427; 424/274, 424/116; 435/117

[56] References Cited

U.S. PATENT DOCUMENTS 4,007,267   2/1977   Kishi et al. ........................... 424/116

Primary Examiner—Arthur P. Demers
Attorney, Agent, or Firm—Fitzpatrick, Cella, Harper & Scinto

[57] ABSTRACT

The antibacterial compound S551-II (Reductiomycin) is produced by culturing a microorganism belonging to the genus Streptomyces.

S551-II-A is prepared by sublimation of the compound S551-II.

5 Claims, 3 Drawing Figures

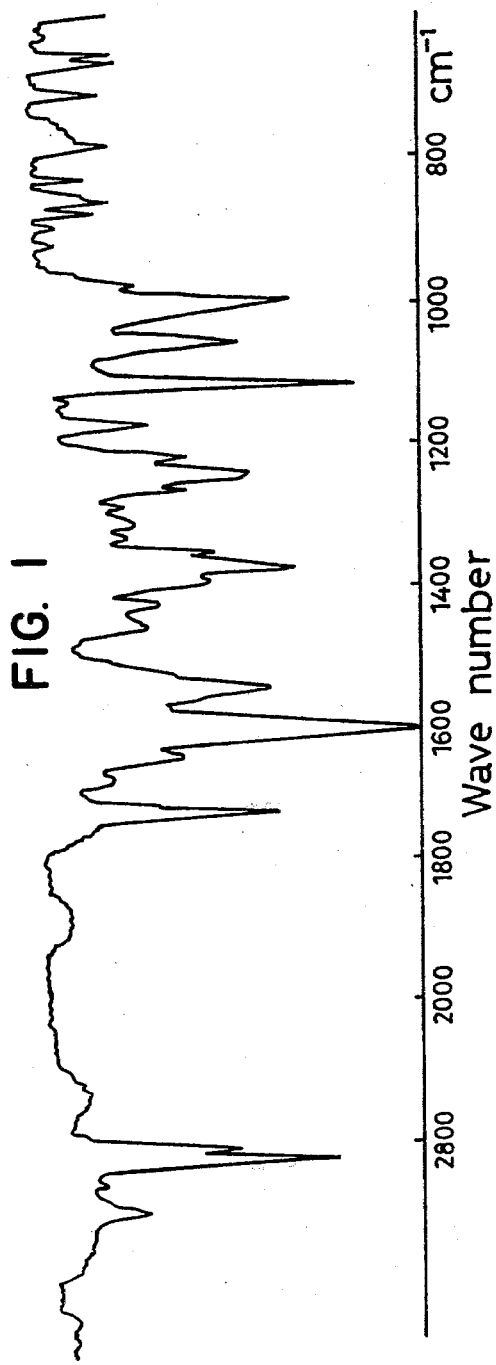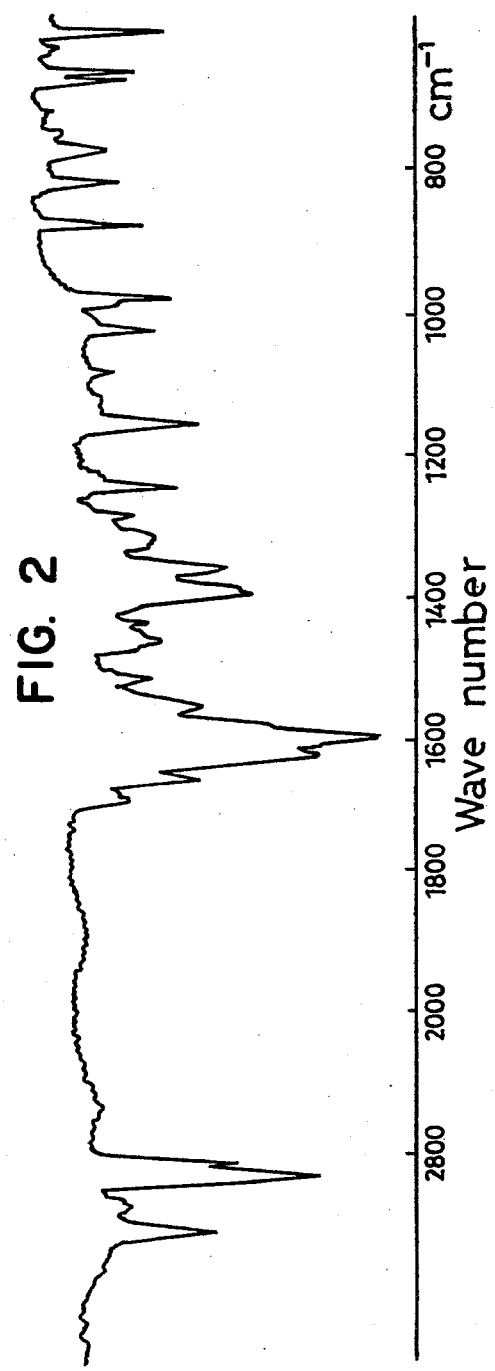

ANTIBACTERIAL COMPOUNDS AND PROCESS FOR PRODUCTION THEREOF

This is a division of application Ser. No. 878,776 filed Feb. 17, 1978.

SUMMARY OF THE INVENTION

The present invention relates to new antibacterial compounds S551-II (Reductiomycin) and S551-II-A. The compound S551-II is produced by culturing a microorganism belonging to the genus Streptomyces in a nutrient medium. The compound S551-II-A is produced by sublimating the compound S551-II.

BRIEF DESCRIPTION OF DRAWINGS

FIG. 1 shows the infrared absorption spectrum of the compound S551-II.

FIG. 2 shows the infrared absorption spectrum of the compound S551-II-A.

DETAILED EXPLANATION OF THE INVENTION

Figure 3:
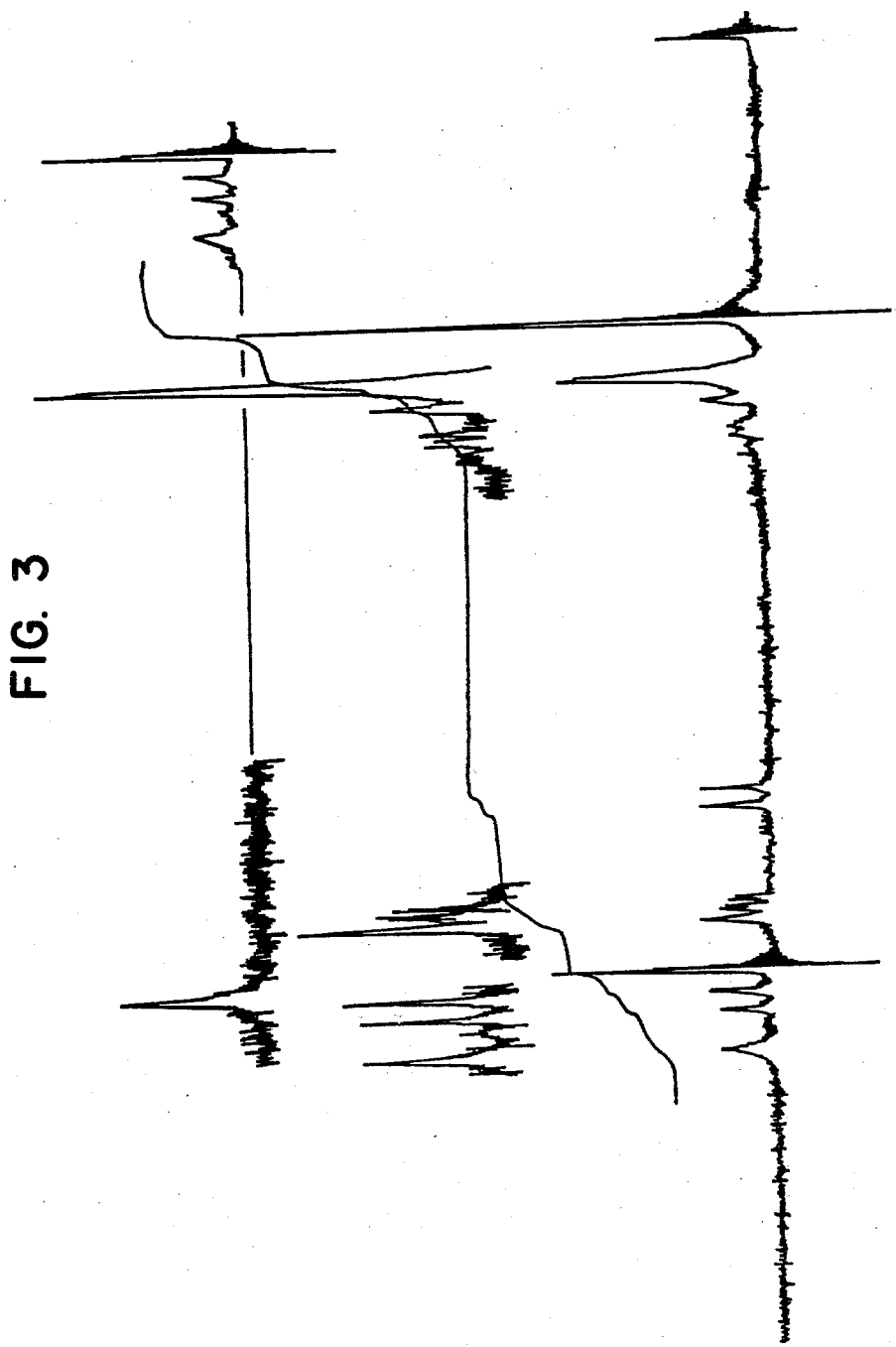
FIG. 3 shows the nuclear magnetic resonance spectrum of the compound S551-II.

The present invention relates to new antibacterial compounds represented by the following general formula:

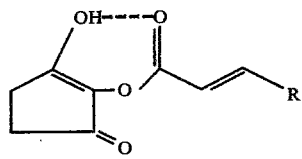

wherein R is 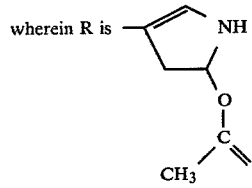

(the compound having the following formula

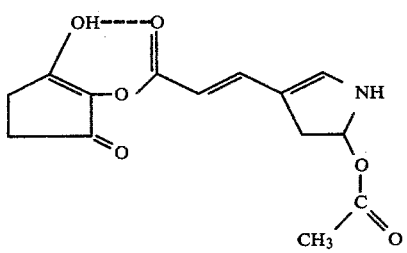

is referred to as Compound S551-II hereinafter) or

R is 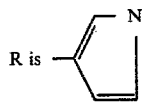

(the compound having the following formula

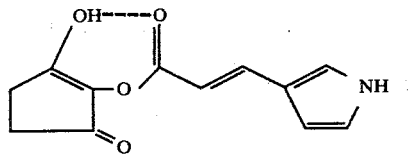

is referred to as S551-II-A hereinafter.).

The compound S551-II is also designated as Reductiomycin.

The antibacterial compound S551-II is produced by culturing a microorganism belonging to the genus Streptomyces and being capable of producing the antibacterial compound in a nutrient medium. The antibacterial compound is accumulated in the culture medium and is isolated therefrom.

The antibacterial compound S551-II-A is produced by sublimation of the compound S551-II.

The present compound S551-II has the following physicochemical properties.

Appearance: A yellow fine crystal.
Melting point: 215° C. (decompose).
$[\alpha]_D^{23°}$: +281° (c=0.30, acetone).
Molecular weight: 293 (by the mass spectrometry).
Elementary analysis: C: 57.36%, H: 5.25%, N: 4.73%.
Molecular formula: $C_{14}H_{15}O_6N$.
Ultraviolet absorption spectrum (the maximum value, $\epsilon$ value): 273 nm (28655) (in methanol); 288 nm (21600) (in 0.1 N HCl-methanol).
Color reactions:
   Ehrlich's reaction (in HCl): positive
   Ferric chloride reaction: positive
   Nitroprusside reaction (in alkaline): positive
   2,4-Dinitrophenylhydrazine reaction: positive
   Pine-shaving reaction: negative
   Ninhydrin reaction: negative
   Schiff's reaction: negative
   Sakaguchi's reaction: negative Infrared absorption spectrum by the paste method is illustrated in FIG. 1.

PMR spectrum measured in $CDCl_3$ by using TMS as an internal standard is illustrated in FIG. 3.

Based on the foregoing data, the compound S551-II is considered to have the structural formula shown earlier.

The compound S551-II-A has the following physicochemical properties.

Appearance: A yellowish crystal
Melting point: 215° C. (sublimate)
$[\alpha]_D^{23°}$: 0° (c=0.30, dimethylsulfoxide)
Molecular weight: 233 (by the mass spectrometry).
Elementary analysis: C: 60.98%, H: 4.59%, N: 6.06%.
Molecular formula: $C_{12}H_{11}O_4N$.
Ultraviolet absorption spectrum (the maximum value, $\epsilon$ value): 260 nm (52900) (in methanol and 0.1 N-NaOH.)
Color reactions:
   Ehrlich's reaction (in HCl): positive
   Ferric chloride reaction: positive
   2,4-dinitrophenylhydrazine reaction: positive
   Ninhydrin reaction: negative
   Schiff's reaction: negative
   Sakaguchi's reaction: negative
   Nitroprusside reaction: negative Solubilities: The compound is soluble in acetone, dimethylsulfoxide and alkaline solution, slightly soluble in methanol and insoluble in bezene, chloroform ethylether and hexane.

Infrared absorption spectrum of S551-II-A by the paste method is illustrated in FIG. 2.

Based on the foreging data, the compound S551-II-A is considered to have the structural formula shown earlier.

Now, the process for producing S551-II is described below.

The new antibacterial compound S551-II is produced by culturing a microorganism belonging to the genus Streptomyces and being capable of producing the compound. A suitable microorganism belongs to *Streptomyces griseorubiginosus*. Its typical strain is *Streptomyces griseorubiginosus* KY 11448 (FERM-P 3836) (NRRL 11,268).

The strain has the following properties.

I. MORPHOLOGY

The spore forming mycelium shows flexous simple branching. A chain of ten or more spores is formed.

The surface of the spore is smooth and the diameter of its minor axis and major axis are $1.0\mu$ and $2.5\mu$, respectively. The sporophore is formed on the aerial mycelium.

II. CULTURE CHARACTERISTICS

| Medium | Growth | Aerial Mycelium | Color of the substrate mycelium | | Soluble pigment |
| --- | --- | --- | --- | --- | --- |
| | | | The surface | The reverse side | |
| Sucrose-nitrate agar | Poor Flat | Poor White(a) | White (a) | White (a) | None |
| Glucose-asparagine agar | Moderate Raised | Moderate Light Ivory (2ca) | Cream (1½a) | Light Yellow (1½ea) | None |
| Glycerin-asparagine agar | Moderate Flat | Moderate Light Ivory (2ca) | Cream (1½a) | Light Yellow (1½ea) | None |
| Starch agar | Good Raised | Good Cream (1½a) | Cream (1½a) | Light Yellow (1½ea) | Butter Yellow (1½ea) |
| Tyrosine agar | Good Raised | Good Cream (1½a) | Dull Gold (2ng) | Mustard Brown (2ni) | Antique Gold (1½ne) |
| Nutrient agar | Good Raised | None | Bright Gold (2nc) | Bright Gold (2nc) | Amber (3pc) |
| Yeast extract-malt extract agar | Good Raised | Good Putty (1½ec) | Golden Brown (3pg) | Golden Brown (3pg) | Mustard Gold (2ne) |
| Oatmeal agar | Good Raised | None | Dull Gold (2ng) | Dull Gold (2ng) | Clove Brown (3ni) |

The color indications are given according to the classifications in the Color Harmony Manual (Container Corporation of America).

III. PHYSIOLOGICAL PROPERTIES

Growth temperature: 25° to 38° C.
Liquefaction of gelatin: negative
Hydrolysis of starch: positive
Coagulation and peptonization of skim milk: negative
Liquefaction of skim milk: positive
Formation of melanoid pigments: positive

IV. UTILIZATION OF CARBON SOURCES

| Carbon source | Utilization |
| --- | --- |
| D-Arabinose | — |
| D-Xylose | — |
| D-Glucose | 2+ |
| D-Fructose | 2+ |
| Sucrose | — |
| Inositol | — |
| L-Rhamnose | — |
| Raffinose | + |
| D-Mannitol | 2+ |

On the basis of the above observations and the description of E. Kuster, International Journal of Systematic Bacteriology 22 (3), 139 (1972), the strain is identified as *Streptomyces griseorubiginosus*.

As the fermentation medium employed in the present process, any synthetic or natural medium can be employed, so long as it contains a proper carbon source, a nitrogen source, inorganic materials and other necessary nutrients for the growth of the microorganism.

As the carbon source, various carbohydrates such as glucose, fructose, sucrose, galactose, xylose, sorbitol, mannitol, glycerol, starch, starch hydrolyzate liquor, molasses, blackstrap molasses, etc., various hydrocarbon such as ethane, propane, butane, n-paraffine, kerosene, etc., various organic acid such as acetic acid, fumaric acid, succinic acid, lactic acid, pyruvic acid and alcohols such as methanol, ethanol, etc. may be used.

As the nitrogen source, aqueous ammonia, various inorganic and organic ammonium salts such as ammonium sulfate, ammonium chloride, ammonium phosphate, ammonium acetate, etc.; urea, acid amides, amines, amino acids, defatted cotton seed, meat extract, yeast extract, corn steep liquor, casein hydrolyzate, fish meal or its digested product, defatted soybean or its digested product, soybean protein hydrolyzate; various microbial cells or its digested product, etc. may be used.

As inorganic materials, dipotassium monohydrogen phosphate, monopotassium dihydrogen phosphate, magnesium sulfate, sodium chloride, ferrous sulfate, manganese sulfate, calcium carbonate, magnesium phosphate, etc. may be used.

If other nutrients are necessary for the growth of the microorganisms used in the present invention, they must, of course, be present in the medium. They are sometimes supplied to the medium together with natural materials exemplified as a nitrogen source.

Culturing is carried out under aerobic conditions such as with shaking or aeration-agitation. Suitable culturing temperature is usually 23° to 38° C. It is desirable to keep the pH of the medium at 3 to 8, preferably around neutrality throughout culturing.

Culturing is usually carried out for 1 to 7 days to accumulate the compound S551-II in the culture liquor.

After completion of the culturing, microbial cells and precipitates are removed from the culture liquor by filtration or centrifugation and the compound S551-II may be recovered and isolated from the resultant solution by combination of ion exchange treatment, column chromatography using silica gel, etc.

The compound S551-II-A is prepared as follows. The compound S551-II is heated at a temperature of 215° or more and is sublimated accompanying with deacetic acid reaction to form compound S551-II-A. The product crystallized on the glass plate was collected and washed with methanol to obtain a pure S551-II-A as crystals.

The antibacterial activity of the compound S551-II against various microorganisms by disc method (pH: no adjustment) is shown in the following Table 1.

Table 1

| Microorganism tested | MIC (mcg/ml) |
|---|---|
| Aspergillus niger IAM 2026 | 250 |
| Aspergillus niger ATCC 6275 | 1,000 |
| Aspergillus oryzae NRRL 692 | 62.5 |
| Penicillium chrysogenum IAM 7142 | 125 |
| Penicillium chrysogenum O 174 | 62.5 |
| Mucor Spinescens IAM 6071 | 500 |
| Dusarium moniliforme IAM 5062 | 125 |
| Myrothecium verrucaria IAM 5063 | 125 |
| Trycophyton mentagrophytes IAM 5064 | 4 |
| Mrycoderma T-1 ATCC 9645 | 16 |
| Chactomium globosum ATCC 6025 | 500 |
| Microsporum gypseum IFO 5948 | 125 |
| Alternaria solani IFO 5924 | 8 |
| Cladosporium herbarum Link Fr IAM 5059 | 31.2 |
| Bacillus subtilis PCI 219 | 62.5 |
| Bacillus subtilis IAM 1026 | 31.2 |
| Bacillus subtilis NA 64 | 62.5 |
| Sarcina lutea IAM 1099 | 125 |
| Staphylococcus aureus FAD 209P | 62.5 |
| Diplococcus pneumoniae | 1000 |
| Escherichia coli IAM 1268 | 1000 |
| Escherichia coli ATCC 3655 | 500 |
| Serratia marcescens IAM 1022 | >1000 |
| Proteus vulgaris HX19 IAM 1025 | >1000 |
| Pseudomonas aeruginosa IAM 1156 | >1000 |
| Pseudomonas fluorescens ATCC 27 | >1000 |
| Salmonella enteritidis | >1000 |
| Shigella sonnei E23 | >100 |
| Klebsiella pneumoniae 348 | >1000 |
| Candida albicans IAM 4888 | >1000 |
| Saccharomyces cerevisiae IAM 4485 | 1000 |
| Saccharomyces rouxii M-9 | 1000 |

The antibacterial activity of the compound S551-II-A against various microorganism by agar dilution method (pH 7.0) is shown in Table 2.

Table 2

| Microorganism tested | MIC (mcg/ml) |
|---|---|
| Bacillus subtilis ATCC 10707 | 200 |
| Staphylococcus aureus ATCC 6538P | 200 |
| Klebsiella pneumoniae ATCC 10031 | 200 |
| Proteus vulgaris ATCC 6897 | 25 |
| Escherichia coli ATCC 3655 | 500 |

As it is obvious from above description, compounds of the present invention are useful to clean and disinfect laboratory glassware and surgical instruments, and may also be used in combination with various soaps for sanitation purposes and in cleaning and sanitizing hospital rooms and areas used for the preparation of food.

Practice of certain specific embodiments of the invention is illustrated by the following representative examples.

EXAMPLE 1

Composition of fermentation medium (as same as seed medium):

| Soluble starch | 2% |
|---|---|
| Gluten meal | 2% |
| Defatted cotton seed | 2% |
| Dry yeast | 2% |
| CaCOhd 3 | 0.3% |
| MgSO$_4$ . 7H$_2$O | 0.07% |
| Silicon K966 | 0.1% (V/V) |

-continued

| (antifoaming agent) |
|---|

Streptomyces griseorubiginosus KY 11448 (FERM-P No. 3836) (NRRL 11,268) is used as a seed strain.

200 ml of seed culture obtained by culturing the above seed strain in 300 ml of seed medium in a Sakaguchi-flask for 50 hrs in advance is transfered into 30 l-Jar containing 15 l of said fermentation medium. Culturing is carried out at 30° C. for 72 hrs with aeration of 14 l/min. and stirring at 300 r.p.m.

After culturing, culture broth is filtrated to remove microbial cells and the filtrate is extracted with about 15 l of ethylacetate. The resulting extract is concentrated to dryness under reduced pressure. The above separated microbial cells is extracted with acetone and the resulting extract is concentrated to dryness under reduced pressure. Then, the obtained residue is ectracted with ethylacetate and concentrated to dryness under reduced pressure. The resulting two residues are collected and is subjected to chromatography using silica gel (200 ml by volume) and then washed with 500 ml of benzene. Then, elution is carried out with each of 500 ml of benzene-methanol (1% by volume), benzene-methanol (2% by volume) and benzene-methanol (3% by volume). The eluates by benzene-methanol are collected and concentrated to dryness and then resulting residue is washed with about 30 ml of ethyletherchloroform (10:1 by volume). Then, recrystallization is carried out twice from about 8 ml of chloroform and about 5 ml of acetone, whereby 30 mg of compound S551-II is obtained as yellow fine crystal.

EXAMPLE 2

Synthesis of compound S551-II-A

Compound S551-II obtained in Example 1 is put on heater and is covered with Petri dish. Then, the compound is heated at 215° C. whereby compound S551-II is sublimated and the volatile component is adhered to wall of Petri dish to form crystals. The resulting crystals are collected and are washed with methanol, whereby pure compound S551-II-A is obtained.

What is claimed is:

1. Compounds represented by the following general formula:

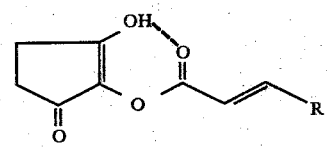

wherein R represents 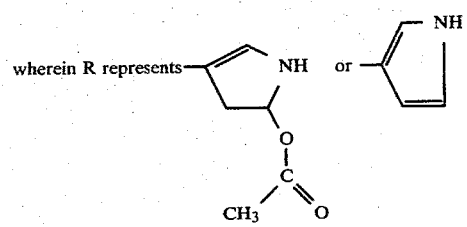

2. Compound S551-II represented by the formula:

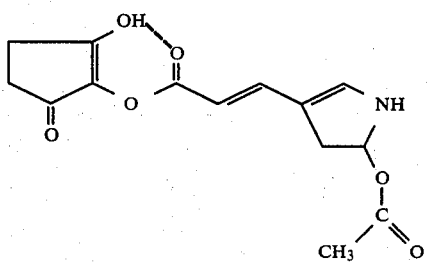
3. Compound S551-II-A represented by the formula:
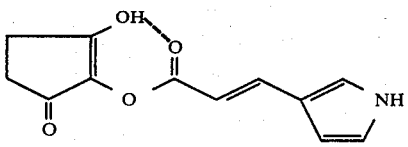
4. A process for preparing compound S551-II-A which comprises sublimating compound S551-II.
5. The process according to claim 4 wherein the sublimation is carried out at a temperature of 215° or more.
* * * * *

UNITED STATES PATENT AND TRADEMARK OFFICE
CERTIFICATE OF CORRECTION

PATENT NO. : 4,221,908

DATED : September 9, 1980

INVENTOR(S) : GAKUZO TAMURA, et al.

It is certified that error appears in the above-identified patent and that said Letters Patent are hereby corrected as shown below:

Col. 3, line 44, under "Soluble pigment" "Butter Yellow (1 1/2 ea)" should be --Butter Yellow (1 1/2 ga)--

Col. 5, Table 1, under "Microorganism tested", "Penicillium Chrysogenum O 174" should be --Penicillium Chrysogenum Q 176--;

Table 1, under "Microorganism tested", "Mrycoderma T-1" should be --Trycoderma T-1--;

Table 1, under "Microorganism tested", "Chactomium globosum" should be --Chaetomium globosum--;

line 67, "CaCOhd3" should be --$CaCO_3$--;

line 69, "Silicon K966" should be --Silicon KS66--.

UNITED STATES PATENT AND TRADEMARK OFFICE
CERTIFICATE OF CORRECTION

PATENT NO. : 4,221,908

DATED : September 9, 1980

INVENTOR(S) : GAKUZO TAMURA, et al.

It is certified that error appears in the above-identified patent and that said Letters Patent are hereby corrected as shown below:

Col. 3, line 54, under "Growth", "Good" should be --Poor--;

Col. 4, lines 48-50 delete "They are sometimes supplied to the medium together with natural materials exemplified as a nitrogen source" and insert --In some cases, these nutrients are added as components of the natural substances in the medium such as the organic nitrogen sources mentioned above.--

Signed and Sealed this

Twentieth Day of January 1981

[SEAL]

Attest:

Attesting Officer

RENE D. TEGTMEYER

Acting Commissioner of Patents and Trademarks